United States Patent [19]
Baer et al.

[11] Patent Number: 5,830,129
[45] Date of Patent: Nov. 3, 1998

[54] PROCESS AND APPARATUS FOR MEASURING BLOOD FLOW THROUGH AN ORGAN OR OTHER BIOLOGICAL TISSUE

[76] Inventors: Hans Baer, Bolleystrasse 12, CH-8006, Zurich; Eduard Hirsbrunner, Clausiusstrasse 67, CH-8006, Zurich; Daniel Flueckiger, Bahnhofstrasse 13, CH-6410, Goldau, all of Switzerland

[21] Appl. No.: 380,313
[22] PCT Filed: Apr. 1, 1993
[86] PCT No.: PCT/CH92/00194
§ 371 Date: May 24, 1993
§ 102(e) Date: May 24, 1993
[87] PCT Pub. No.: WO93/05700
PCT Pub. Date: Apr. 1, 1993

Related U.S. Application Data

[63] Continuation of Ser. No. 64,124, May 24, 1993, abandoned.

[30] Foreign Application Priority Data
Sep. 26, 1991 [CH] Switzerland .................. 02860/91

[51] Int. Cl.$^6$ .................................................. A61B 5/00
[52] U.S. Cl. ..................... 600/300; 600/485; 600/481; 600/504; 600/500; 600/561; 600/549; 600/309; 600/322
[58] Field of Search .................... 128/633, 652, 128/630, 632, 664–7, 672, 663, 673, 675, 680–3, 687, 690, 691, 692, 696, 713, 736, 748

[56] References Cited

U.S. PATENT DOCUMENTS

| | | |
|---|---|---|
| 3,249,103 | 5/1966 | Woodhouse . |
| 4,200,109 | 4/1980 | McMorrow, Jr. . |
| 4,407,272 | 10/1983 | Yamaguchi . |
| 4,481,804 | 11/1984 | Eberhard et al. . |
| 4,621,643 | 11/1986 | New, Jr. et al. . |
| 4,700,708 | 10/1987 | New, Jr. et al. ....................... 128/635 |
| 4,770,179 | 9/1988 | New, Jr. et al. . |
| 5,252,962 | 10/1993 | Urbas et al. ........................... 128/903 |

FOREIGN PATENT DOCUMENTS

| | | |
|---|---|---|
| 0049477 | 4/1982 | European Pat. Off. . |
| 0074498 | 3/1983 | European Pat. Off. . |
| 0103185 | 3/1984 | European Pat. Off. . |
| 0104772 | 4/1984 | European Pat. Off. . |
| 0452276 | 10/1991 | European Pat. Off. . |
| 9306776 | 4/1993 | WIPO .................................... 128/692 |

OTHER PUBLICATIONS

Knut Aukland et al., "Measurement of Local Blood Flow with Hydrogen Gas", Circulation Research, vol. XIV, Feb. 1964.

Wise Young et al., H2 Clearance Measurement of Blood Flow: A Review of Technique and Polarographic Principles, in *Stroke*, vol. 11, No. 5, Sep.–Oct. 1980, pp. 552–564.

International Search Report and Annex.

B.C. Dillon et al., "Externally Powered Semiconductor Transponder", vol. 20, No.7 Dec. 1977.

*Primary Examiner*—Robert L. Nasser
*Attorney, Agent, or Firm*—Greenblum & Bernstein P.L.C.

[57] ABSTRACT

A process for measuring parameters of organs and tissues, especially blood flow through an organ, particularly the liver, is based on a medical technology apparatus that can be constructed in modular fashion. The preferred process uses the hydrogen clearance method to determine blood flow. The preferred apparatus includes at least one measuring instrument and at least one measuring or therapy sensor that is detachable from that instrument. Additional connecting elements make it possible to construct an individually adapted measurement array. For a monitoring and checking operation, both the sensors or therapy heads, and the various connecting elements are equipped with electronic code elements which can be systematically read and evaluated by at least one of the measuring instruments used.

11 Claims, 15 Drawing Sheets

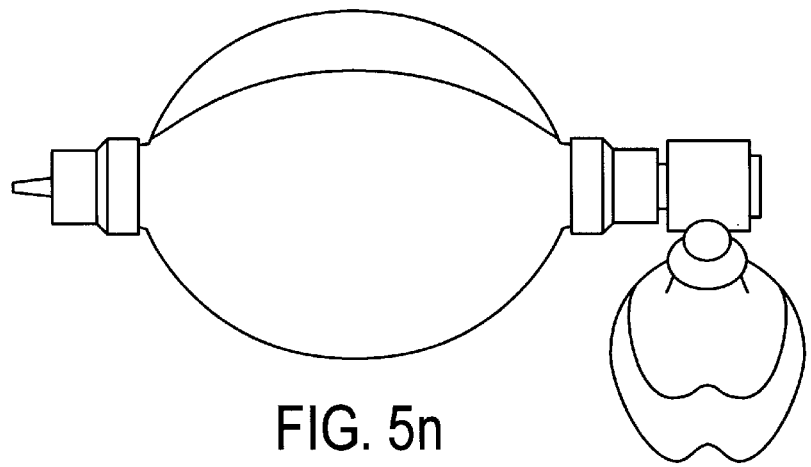
FIG. 5n
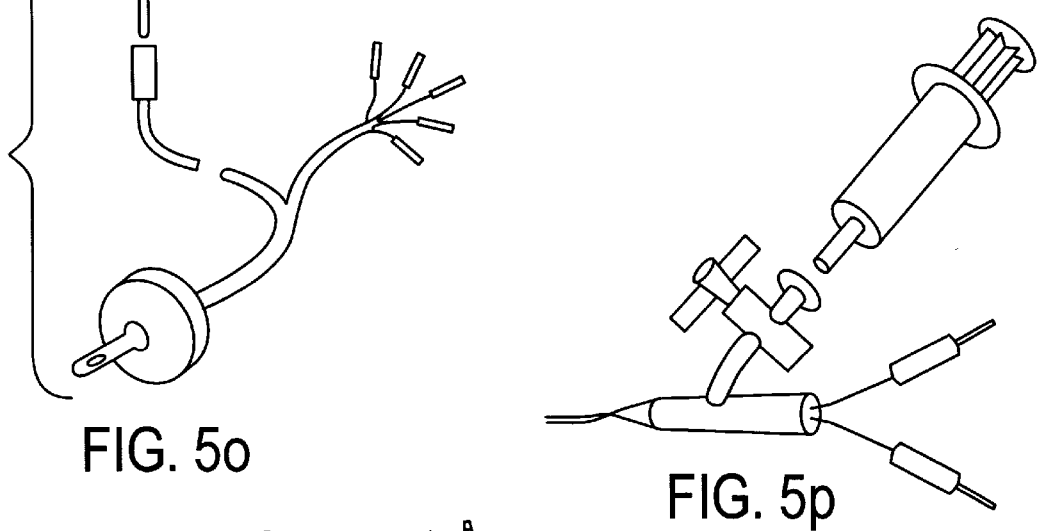
FIG. 5o
FIG. 5p
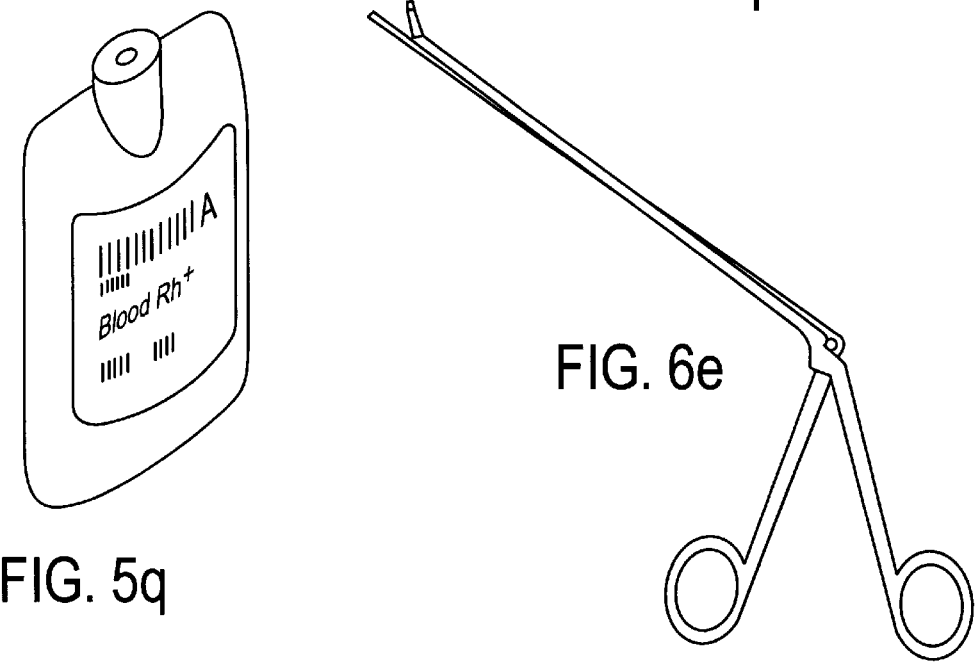
FIG. 5q
FIG. 6e

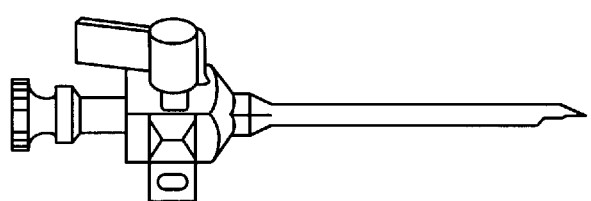
FIG. 6a
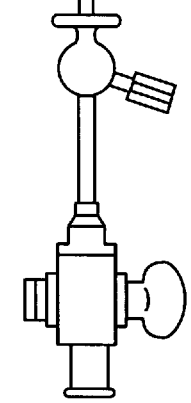
FIG. 6b
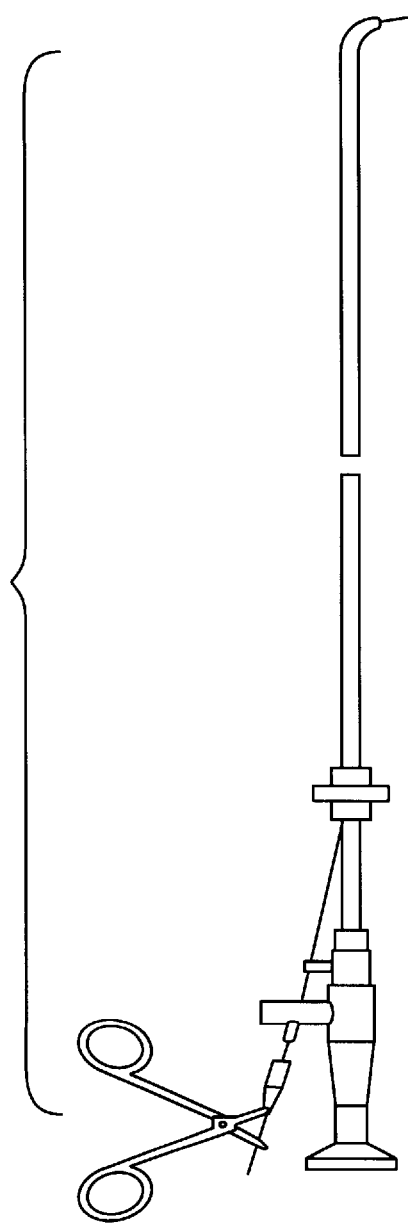
FIG. 6c
FIG. 6d

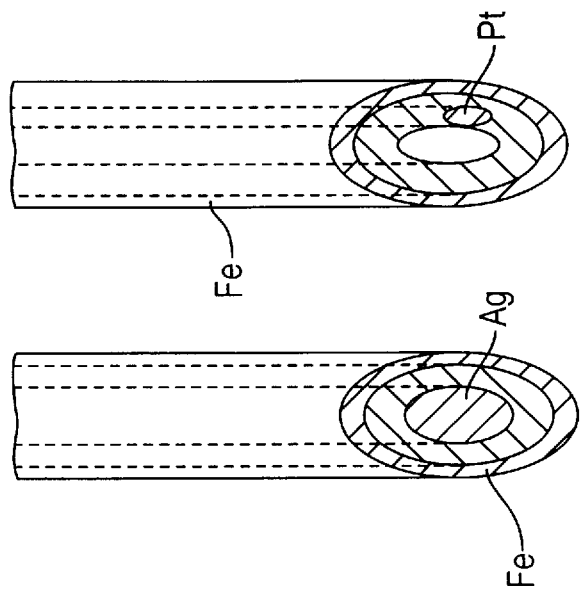
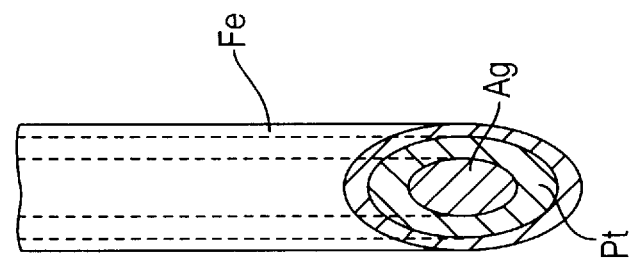
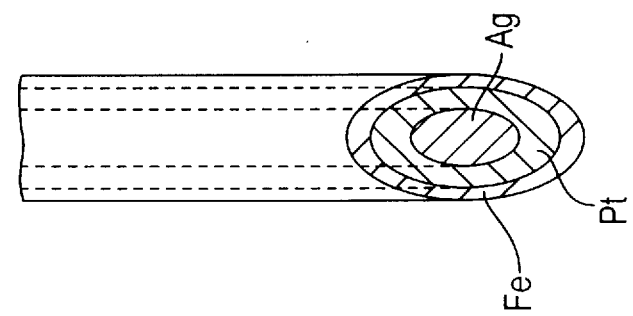
FIG. 6f(1)   FIG. 6f(2)   FIG. 6g(1)   FIG. 6g(2)

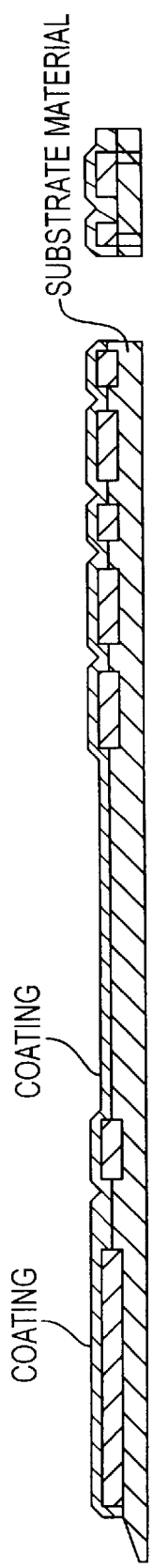
FIG. 6h(1)
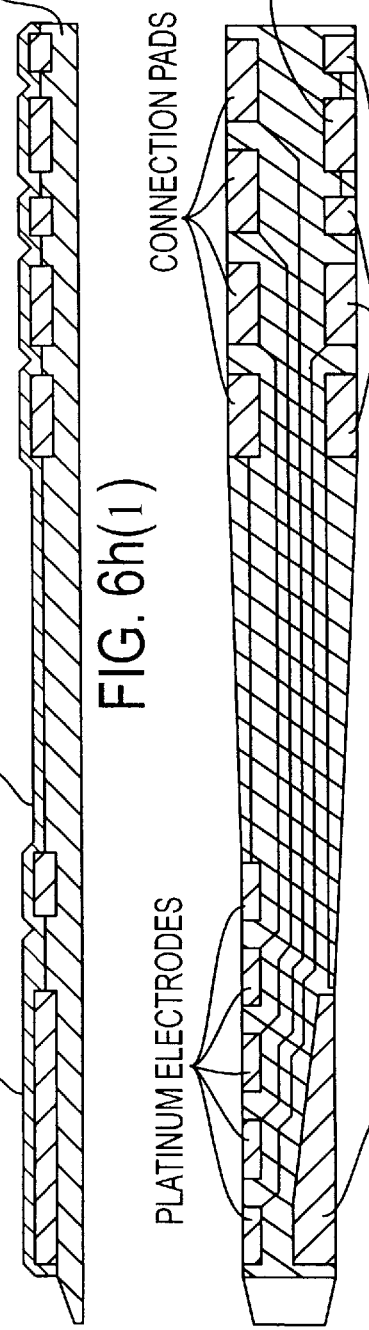
FIG. 6h(3)
FIG. 6h(4)
FIG. 6h(2)
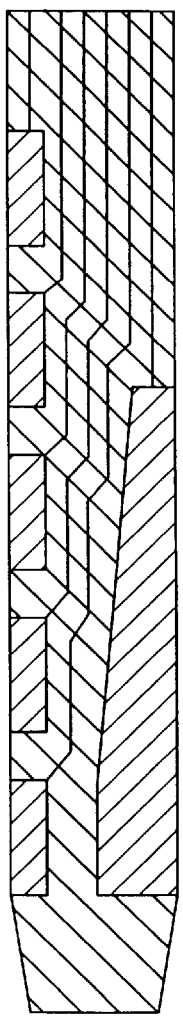
FIG. 6h(6)
FIG. 6h(5)

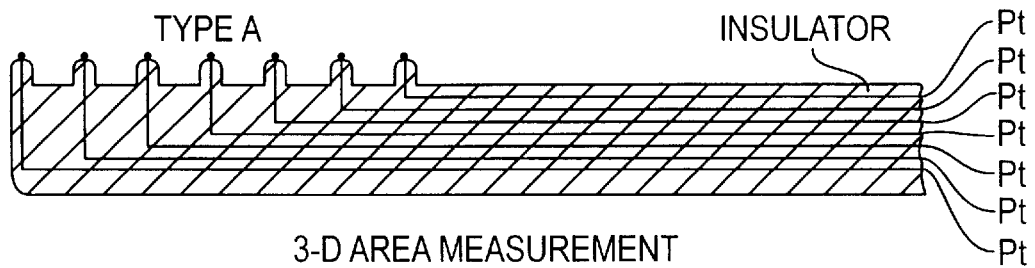
FIG. 6i(1)
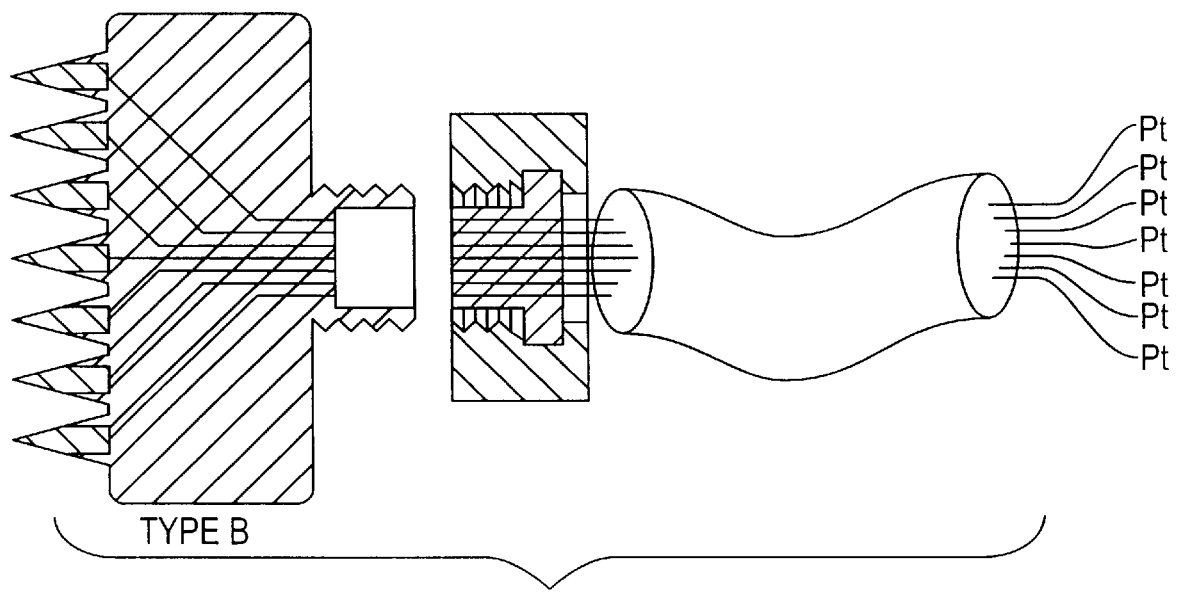
FIG. 6i(2)

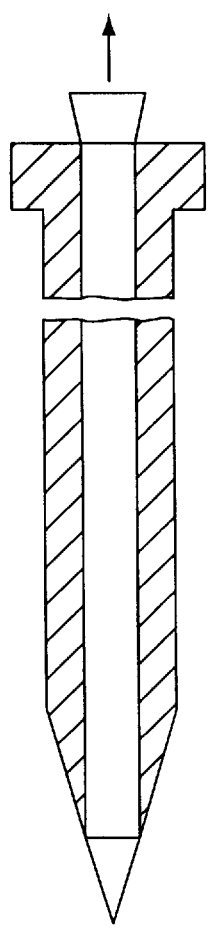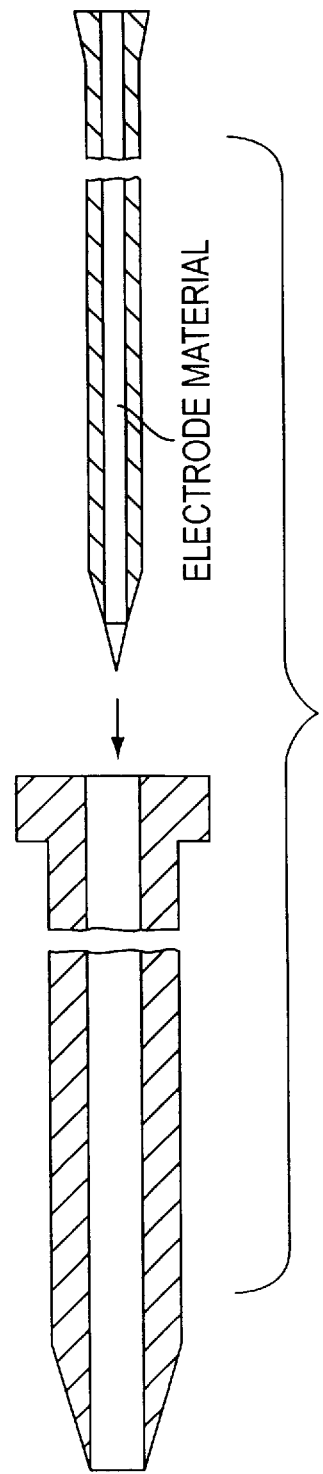
FIG. 6k(1)
FIG. 6k(2)
ELECTRODE MATERIAL

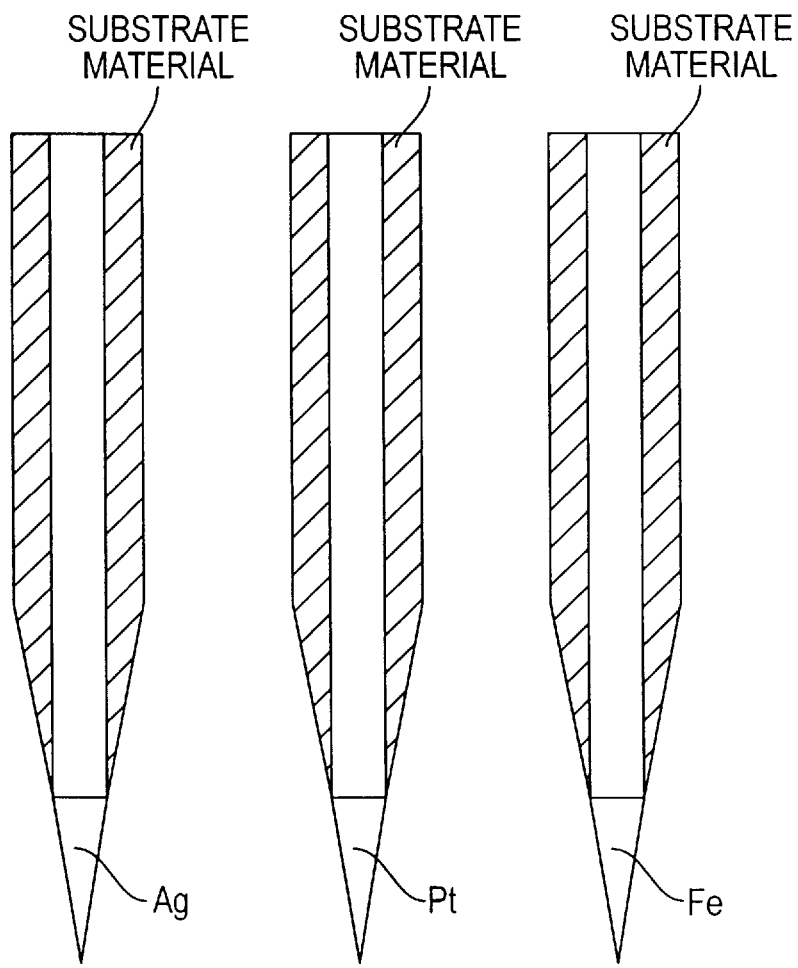
FIG. 6l(1)   FIG. 6l(2)   FIG. 6l(3)

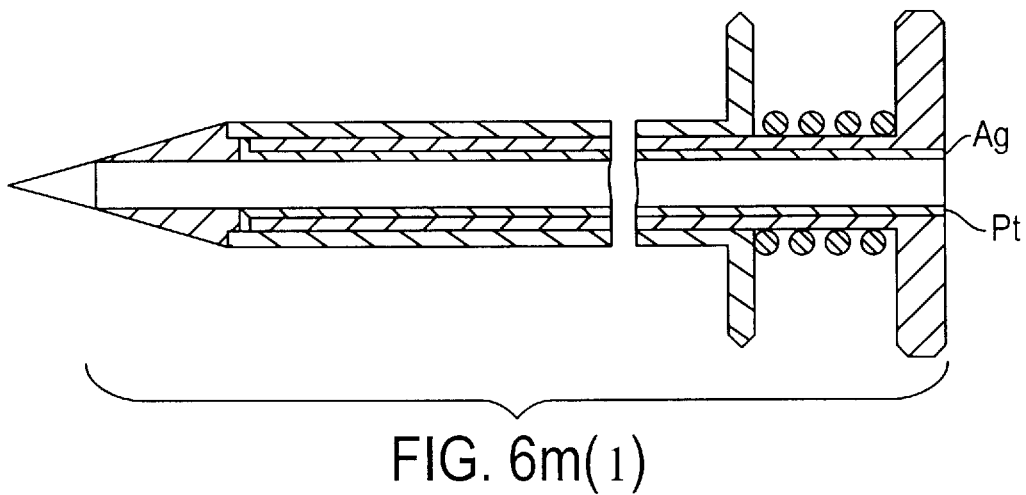
FIG. 6m(1)
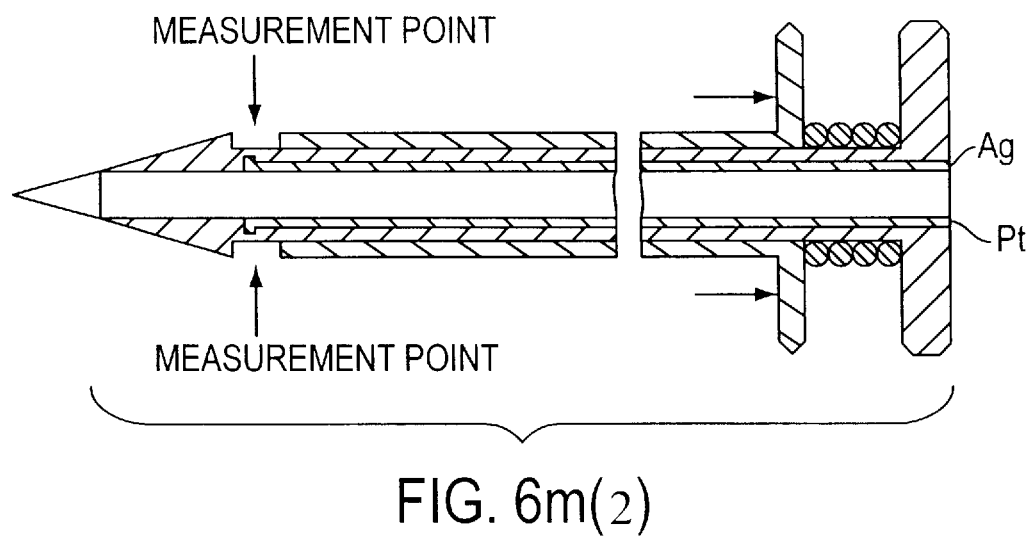
FIG. 6m(2)

PROCESS AND APPARATUS FOR MEASURING BLOOD FLOW THROUGH AN ORGAN OR OTHER BIOLOGICAL TISSUE

This application is a continuation of application No. 08/064,124, filed May 24, 1993, now abandoned, which is the National Phase of PCT/CH92/00194, filed Sep. 25, 1993.

BACKGROUND OF THE INVENTION

1. Field of the Invention

The present invention relates to a process for measuring the blood flow in or through an organ, particularly in human tissue, employing the hydrogen clearance method, and suitable means for performing this process.

2. Background and Material Information

Processes and measuring instruments for measurement of blood flow through an organ are known in the medical field and function both as a diagnostic tool, as well as for monitoring of the course and success of therapy or of a surgical operation. In known processes, the blood of the subject is enriched with hydrogen and used as an electrolyte, and two electrodes are introduced into the tissue to be studied to form a galvanic element. The electrical voltage of this element is related to the concentration of the hydrogen in the blood, among other factors. Hydrogen is mixed with air and introduced into the blood via the respiratory tract or, alternatively, hydrogen may be injected directly into the blood stream. As soon as the voltage between the electrodes has attained a predetermined limit value, the delivery of hydrogen is discontinued and a decrease in voltage as a function of time is observed. The slope of the measured curve of this function is representative of a measure for the tissue blood flow, in which the hydrogen-enriched blood is removed and replaced by hydrogen-free blood. The theoretical bases of this process, and in particular the calculation of the potentials of the electrodes as a function of the hydrogen ion concentration with the aid of Nernst's equation and the determination of the blood flow of a tissue volume from the decrease in concentration of the hydrogen in the blood with the aid of diffusion principles, are described in detail, for instance by K. Auckland et al, in Circulation Research, Vol. 14, 1964, pp. 164 ff.

Although determining the blood flow of tissue with the aid of inert gases such as hydrogen has been known for at least 40 years and has been discussed in many publications, the practical application of this process was previously limited to animal experimentation, or to measuring the blood flow rate at the tip of the little finger of a human being. The reasons for this are simple. With the equipment previously used to perform the process described, evaluatable and reproducible measurements could be obtained only if the current intensity between the electrodes and hence in the blood as well, that is, in the tissue to be studied, was at least $1 \times 10^{-6}$ A, a value which is physiologically objectionable or even impermissible for some tissues.

One such measuring instrument is described, for instance, in the article entitled "$H_2$ Clearance Measurement of Blood Flow: A Review of Technique and Polarographic Principles", Wise Young, in STROKE, Vol. 11, No. 5, September-October 1980, pp. 552–564.

An apparatus with which, for the first time, the determination of tissue blood flow by the advantageous hydrogen clearance method can be used without the requirement for a measuring current that is physiologically objectionable for human beings, is described in European Patent Application 0 452 276, for example.

Although the process described in EP 0 452 276 is a suitable method for measuring the blood flow in human tissue, it has been found in practice that, during long-term measurements, the highly sensitive electrodes required for this process relatively quickly either become coated with endogenous (especially fibrin-containing) substances, or oxidize, thereby impairing the accuracy of blood flow measurements made over a long period of time.

Another problem arises in the measurement of the spatial distribution of the blood flow in the tissue to be studied, which is especially desirable for long-term measurements. In such a measurement, multiple sensors are introduced into the tissue at multiple spatially separated points. If usable results are to be attained, several measuring instruments are required, and this undesirably raises the cost of the procedure for evaluation of the measured values scanned by the various sensors. Particularly in long-term measurements, this spatial measurement is made more difficult by the repeated insertion of new sensors and the requirement to calibrate these newly inserted sensors. The insertion of new sensors at predetermined points in an organ to be studied involves undesirably high expenses, not only for equipment, but because the procedure can only be carried out by suitably trained physicians. Further, because of the great number of measuring electrodes available, technically untrained persons often use the wrong electrodes and/or inappropriate electrodes for the particular equipment, which makes the measurements inaccurate.

In professional circles, the need therefore exists to create a process and means for performing this process that do not have these disadvantages and with which long-term measurements in particular can be carried out with high measuring accuracy, in a simple and reliable way, even with spatial measurements.

SUMMARY OF THE INVENTION

The object of the present invention is therefore to create a process for measuring the blood flow by the hydrogen clearance method that overcomes the above-mentioned known disadvantages. In particular, it is an object of the invention to make possible reproducible, long-term measurements with multiple sensors which can be safely manipulated.

Another object of the present operating process is to make it possible to monitor whether the various sensors are operative and whether there is an adequate connection between the measuring instrument and each of the sensors. A further object of the invention is the capability of operating these sensors simultaneously with a single measuring instrument.

The above objects are attained by the present invention, which envisages a process of the type discussed at the outset and which includes: placing at least one detachable, coded sensor having at least one electrode or measuring head in the region of a tissue to be studied; connecting the at least one coded sensor to a measuring instrument via at least one coded connecting element; checking and reading at least one code value of the at least one coded sensor using the measuring instrument; performing at least one first measurement of a parameter of the tissue; and storing at least one measured value obtained by the aforesaid at least one first measurement, together with the at least one associated code value, in memory.

The process may further include the step of leaving the at least one sensor in place in the tissue, after performing the at least one measurement; repeating the checking and reading of at lease one code value of the at least one coded sensor at regular time intervals; and, after a desired period of time, performing at least one second measurement.

The process may still further include the step of replacing the at least one electrode or measuring head with at least one unused electrode or measuring head in the region of the tissue to be studied, prior to performing the at least one second measurement.

A preferred embodiment of the measuring instrument includes: a power supply; an analog measuring part comprising a therapy part having at least one coded sensor wherein the at least one sensor has at least one electrode or measuring head for placement in a tissue to be studied, and at least one coded connecting element connecting said at least one coded sensor to said measuring instrument; and a digital part for evaluation and display of measured values; with the analog measuring part further including means for generating a potential in the tissue to be studied, wherein the potential is opposite of inductively or capacitively coupled-in potential fluctuations, and means for reading, checking and storing in memory, at least one code connected to the at least one coded sensor or at least one code connected to the at least one coded connecting elements.

Still further, the analog measuring part may include a measured value and code value detection unit, which periodically scans signals sent from the at least one coded sensor or coded connecting element.

Preferably, the therapy part includes at least one detachable coded sensor.

Preferably, the analog measuring part is galvanically separated from other parts of the measuring instrument.

A preferred embodiment of a measuring instrument is disclosed to include a power supply; an analog measuring part having a therapy part which has at least one coded sensor wherein the at least one sensor has at least one electrode or measuring head for placement in a tissue to be studied; at least one coded connecting element connecting the at least one coded sensor to the measuring instrument; and a digital part for evaluation and display of measured values;

the analog measuring part further includes means for generating a potential in the tissue to be studied, wherein the potential is opposite of inductively or capacitively coupled-in potential fluctuations, and means for reading, checking, and storing in memory, at least one code connected to the at least one coded sensor or at least one code connected to the at least one coded connecting element.

The connecting element may be part of a medical technology utensil.

An electrical resistor element may be used for generating the at least one recognizable code for a coded sensor and/or connecting element.

Further, a microchip may be used for storing the at least one recognizable code. Still further, a transponder may be used for sending the at least one recognizable code.

Further yet, an electrooptical component may be used for storing and/or sending the at least one recognizable code.

Preferably, a coded sensor is disclosed for use in combination with an associated code value detection unit in a process for operating medical technology apparatus comprising the steps of:

a) placing at least one detachable, coded sensor having at least one electrode or measuring head in the region of a tissue to be studied;

b) connecting the at least one coded sensor to a measuring instrument via at least one coded connecting element;

c) checking and reading at least one code value of the at least one coded sensor by said measuring instrument;

d) performing at least one first measurement of a parameter of the tissue; and e) storing at least one measured value obtained by said at least one first measurement, together with the at least one associated code value, in memory, wherein the preferred coded sensor includes an electrode or measuring head carrier; and an electrode or measuring head substrate; and the coded sensor further includes at least one code recognizable by the associated code value detection unit.

Further, the coded sensor may include an electrical resistor element for storing and sending the at least one recognizable code.

Further, the coded sensor may include a microchip for storing the at least one recognizable code. At least a part of an electronic circuitry used by the associated code value detection unit may be located in the coded sensor.

Still further, the coded sensor may include a transponder for sending the at least one recognizable code. At least a part of an electronic circuitry used by the associated code value detection unit may be located in the coded sensor.

Further yet, the coded sensor may include an electrooptical component for storing and/or sending at least one recognizable code.

Preferably, at least part of an electronic circuitry used by the associated code value detection unit is located in the coded sensor.

In a preferred embodiment the electrode or measuring head carrier of the coded sensor comprises a medical technology instrument.

The coded sensor may comprise a plurality of electrodes or measuring heads.

A preferred process of the invention may further include the step of displaying or sending the at least one measured value and associated code value for evaluation.

In particular, the process according to the invention envisages the use of interchangeable sensors which may be of varying types, and/or-the connection of elements or other medical technology utensils, which are inseparably provided with codes, to enable monitoring their identifying characteristics and specification (e.g., origin, age, and type), so that in the assembled state, when ready for use, their proper connection can be monitored, or so that they can be operated by a single measuring instrument and/or therapeutic equipment. Additionally, coding of the sensors and elements enables anterograde and/or retrograde functional control and monitoring.

The advantages attained by the invention substantially increase functional reliability and, hence, patient safety, since monitoring of all the contacts and functions between the measuring instrument and the arbitrarily disposed sensors, medical technology instruments or utensils is made possible. Further, long-term measurements may be performed with increased accuracy and multidimensional display of the values measured by the modular construction of the invention improves quality assurance and increases versatility.

In addition, the sensors and/or connecting elements may feed back or transmit stored or measured information. This mode of operation also enables purposeful control of special functions of the sensors and/or connecting elements.

A measuring instrument, or a monitor which is suitable for performing the process of the present invention includes a power supply; an analog measuring part having a therapy part having at least one coded sensor wherein the at least one sensor has at least one electrode or measuring head for placement in a tissue to be studied, and at least one coded connecting element connecting the at least one coded sensor to the measuring instrument.

Additionally included is a digital part for evaluation and display of measured values. The analog measuring part further includes means for generating a potential in the tissue to be studied, wherein the potential is opposite of inductively or capacitively coupled-in potential fluctuations. Further provided are means for reading, checking and storing in memory, at least one code connected to the at least one coded sensor or at least one code connected to the at least one coded connecting element.

Essentially, a measuring electrode and a reference electrode are provided, and are formed of metals, the intrinsic chemical potentials of which are close to one another. In order to make use of the difference between the aforementioned potentials, both the measuring electrode and the reference electrode are connected via suitable supply leads to the inputs of an operational amplifier. The measuring electrode, the reference electrode and a neutral electrode, with their supply leads, are shielded against external disturbance fields. To induce an opposite potential in the tissue compared with inductively or capacitively coupled potential fluctuations, the shields of the measuring and reference electrodes are connected, by their supply leads, to the neutral electrode via the positive input of a voltage amplifier circuit, and the negative input of the voltage amplifier circuit is connected to a voltage divider for forming the mean value of the potential between the measuring electrode and reference electrode with the reference electrode being connected between the supply leads of these electrodes.

When using a plurality of sensors, particularly for measuring the spatial distribution of blood flow in an organ, the measuring instrument is preferably equipped with an electronic multiplexer, with which the voltage applied to the various sensors is scanned in succession, for example, at a rate of five times per second.

Since the measuring part of the instrument is galvanically separate from the other parts of the instrument, this apparatus makes it possible to perform the hydrogen clearance method for determining blood flow using physiologically unobjectionable current intensities and in a reproducible manner.

Important for enforcing safety and reliability, each component is provided with a code which is detectable by the aforementioned measuring instrument. These codes may be provided with the aid of electronic, electromagnetic or optical structural elements. It will be understood that to enhance patient safety, these encoded components may be affixed to all the medical technology utensils needed or desired for the study. In any case, however, the sensors necessary for the process of the invention and their connecting elements must be inseparably provided with such codes. Further preferred characteristics of the process according to the invention and of the means for performing this process are recited in the claims.

BRIEF DESCRIPTION OF THE DRAWINGS

The invention will be described in further detail below with reference to the accompanying drawings, in which.

DETAILED DESCRIPTION OF THE PREFERRED EMBODIMENTS

Figure 1:
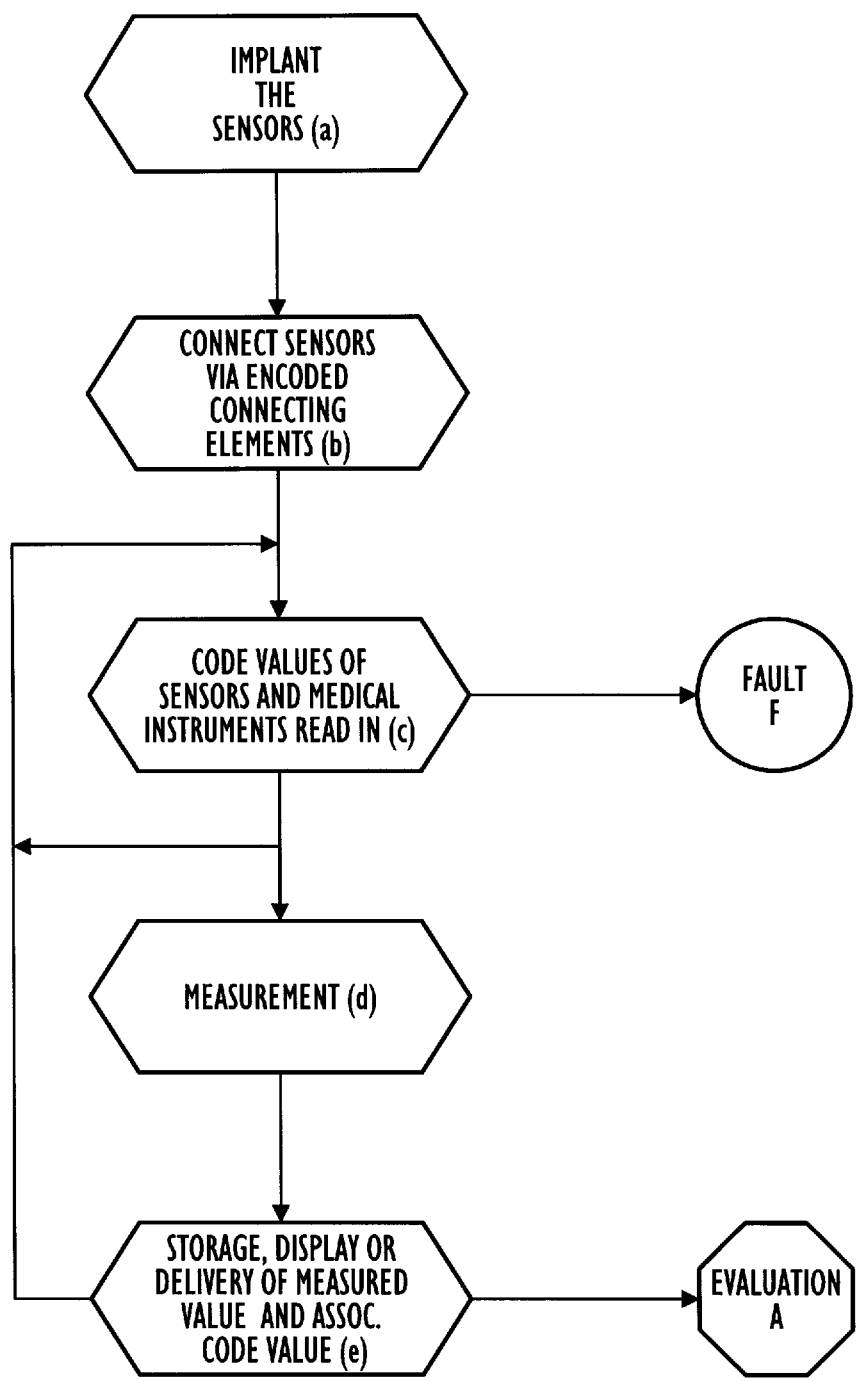
FIG. 1 is a flow chart showing method steps according to the instant invention.

In FIG. 1, the various steps in the present process are assembled into a flow chart. To measure the spatial distribution of blood flow in a human organ, according to the invention, in a step a), a plurality of detachable, individually encoded sensors are implanted, in spatially distributed fashion, in a tissue to be studied. As a rule, this step is carried out by an experienced physician. In a second step b) the various sensors, now implanted are connected via encoded connecting elements to a measuring instrument for determining the blood flow rate by the hydrogen clearance method, The present invention enables step (b) to be carried out even by semiskilled assistants. In step (c), the various code values of the sensors, connecting elements, and other general medical utensils used, are read and checked by the measuring instrument. Upon detection of a faulty connection the measuring instrument displays a fault report F. If the measuring instrument does not detect a faulty connection during the checking Procedure, the measured value detection unit is enabled to defect signals at the measuring electrodes. Simultaneously with the measurement (d), the measured values, along with the associated code values, are stored in memory, displayed, or delivered for evaluation A.

Particularly, once a first measurement has been made, the sensors can be left in the tissue and method step (c) can be repeated, for example, at regulars intervals. After a desired period of time, a further measurement can be made, preferably by the hydrogen clearance method. The measured values from the process are then subjected to evaluation A.

Figure 2:
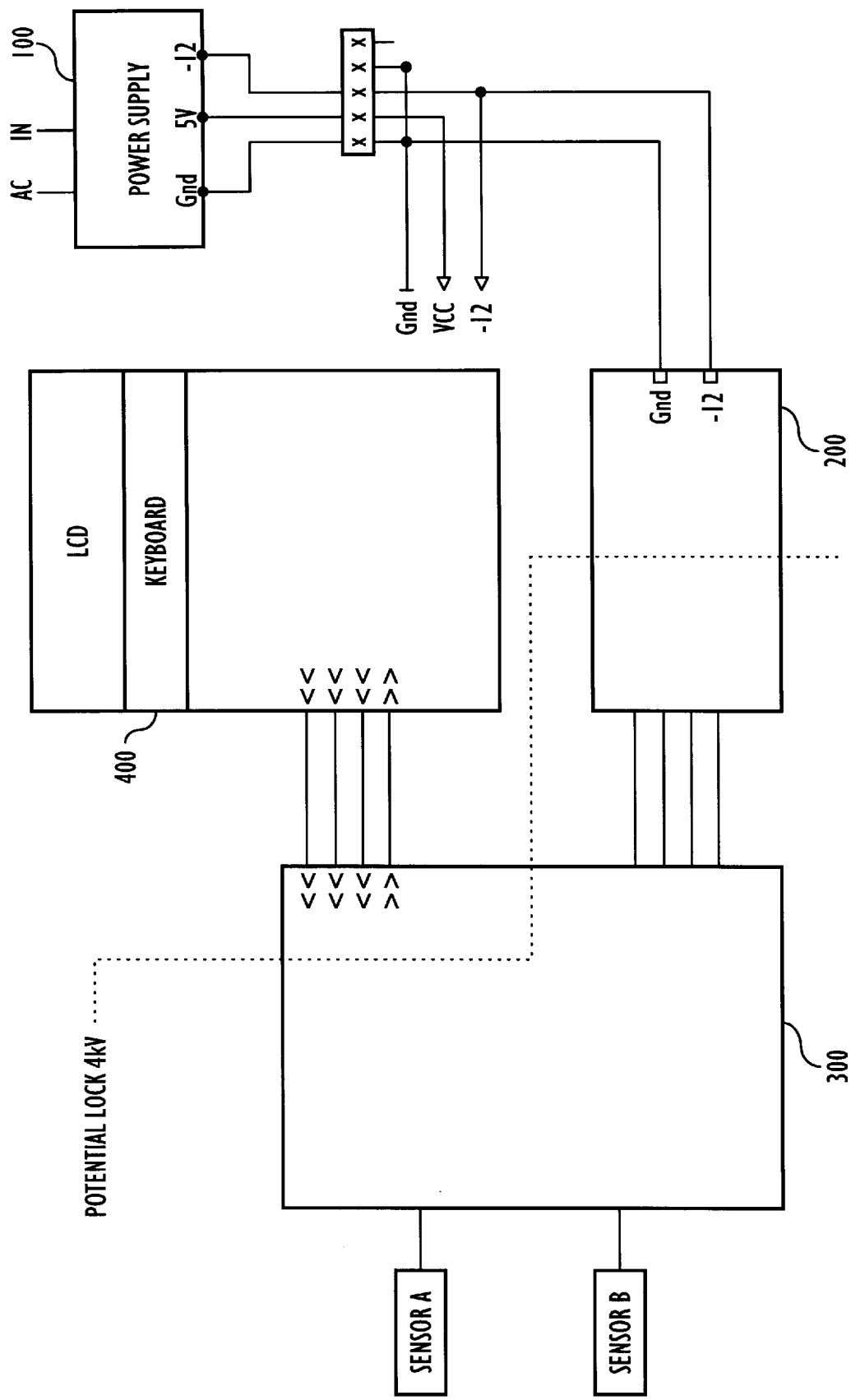
FIG. 2 is a block circuit diagram of a measuring instrument suitable for performing a process according to the instant invention.

The block circuit diagram in FIG. 2 shows a power supply 100 that is connected to a power source 200 that has a potential lock of at least 4 kW and supplies an analog part 300 with the necessary voltage. The sensors A and B, which include at least one electrode each, and which may include an electrical resistor element, a microchip, a transponder, and/or an electroptical component for storing and/or sending a recognizable code, are connected to the analog part 300. A galvanically separate output of the analog part 300 is connected to a digital part 400.

For long-term measurements, catheter-like sensors are implanted, through the cannulas of which electrodes necessary for the desired measurement are introduced, preferably with a needle or inserter. Certain types of electrodes may be removed and/or replaced after a measurement series has been performed. Unsoiled electrodes can be provided for repeated measurements by successively replacing the electrodes between measurements.

The process directed in the flow chart of FIG. 1 may also be carried out using other measurement and therapy techniques, such as $O_2$, pH, glucose, potassium, temperature, blood pressure and intracranial pressure measurements, as well as for medication-infusion equipment.

Figure 3:
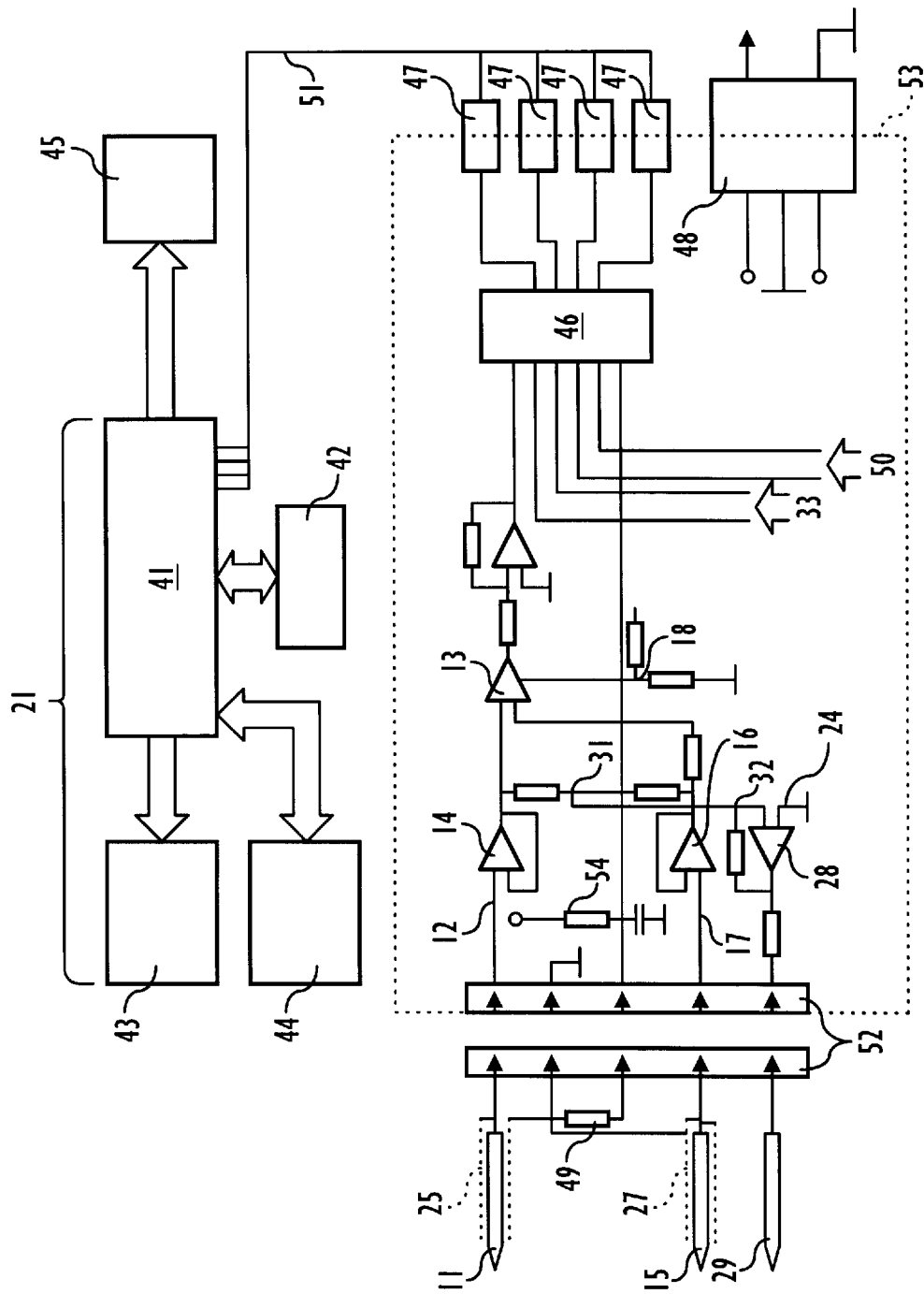
FIG. 3 is a circuit diagram of an analog or measuring part of a measuring instrument suitable for performing a process according to the present invention.

FIG. 3 shows the measuring part of a measuring instrument suitable for performing a process according to the present invention. The measured value detection unit 46 is essential to the invention and is connected to a sensor plug 52. The fixed resistor 54, together with the grounded coding resistor 49, form a voltage divider, the value of which is recognized by the measured value detection unit 46.

In this embodiment, the measuring electrode 11, shielded by shielding 25 from external disturbance potentials, is connected, via a supply lead 12, to a first impedance converter 14, whose output is connected to the negative input of a measuring amplifier 13. A reference electrode 15, shielded by shielding 27, is connected, via a supply lead 17, to a second impedance converter 16, whose output is connected to the positive input of the measuring amplifier 13, via a resistor that is variable for zero balancing.

The preferred measuring instrument also has a driving neutral electrode 29, with which opposed fields are actively coupled into the measuring amplifier 13 in order to compensate for external disturbance fields. To this end, the mean value of all the signals from the voltage divider 31 is kept at 0 V by varying the common ground. The ground feedback via inverting amplifier 28 or via a PI controller is done with high impedance, for instance with an impedance of 100 k$\Omega$. The supply lead 24 for the disturbance voltages is in communication with the shields 25, 27. The output of the differential amplifier 13 is connected to an analog/digital converter 46 via a low-pass filter. The component 46 shown in FIG. 3 detects six signals and has a 10-byte resolution (1024 component). Alternatively, higher-resolution components, such as 4096 (12 byte) components may be used. Triggering on the digital side is done by a microprocessor 41 via a data bus 51 having at least four leads that are connected via optical coupler 47 to the A/D converter. 46. For the supply, a suitable repeating coil 48 is provided.

The free analog inputs 33, 50 can be used to detect other signals, such as signals representing pH value, temperature, or codes. Via the four digital leads 51, signals can be transferred to the analog part simply, using the same connections. The transfer is done serially and may be expanded at will. For instance, the controller may be used to control current for $H_2$ production, perform a switchover of measurement range, or vary OFFSET and amplification of signal detection. The digital part primarily includes the processor 41, and an EPROM 42, which stores the operating program of the processor in memory.

A timer and an 8- to 32-kilobyte RAM memory is also provided, the operation of which is backed up with a built-in battery. In the RAM, a plurality of measurements can be stored and called up again later. The interface components for the display 43, serial interface 45, keyboard 44 and converters are well-known to one skilled in the art. For the display, LCDs or complete monitors can be used equally well. Acoustical warning signals may also be built in.

In a preferred embodiment, the voltage of the sensors is measured at a frequency of 5 times per second. The current value is calculated from that and shown in the display. In addition, the signal of the sensor is read and stored in the nonvolatile memory and made available for evaluation. Preferably, for further illumination of disturbances in the measured values, the mean value of the exponential regression is calculated from 5 to 10 measured values.

This apparatus is equally suitable for flow measurement in veterinary medicine, laboratory work, and industrial applications.

Figure 4:
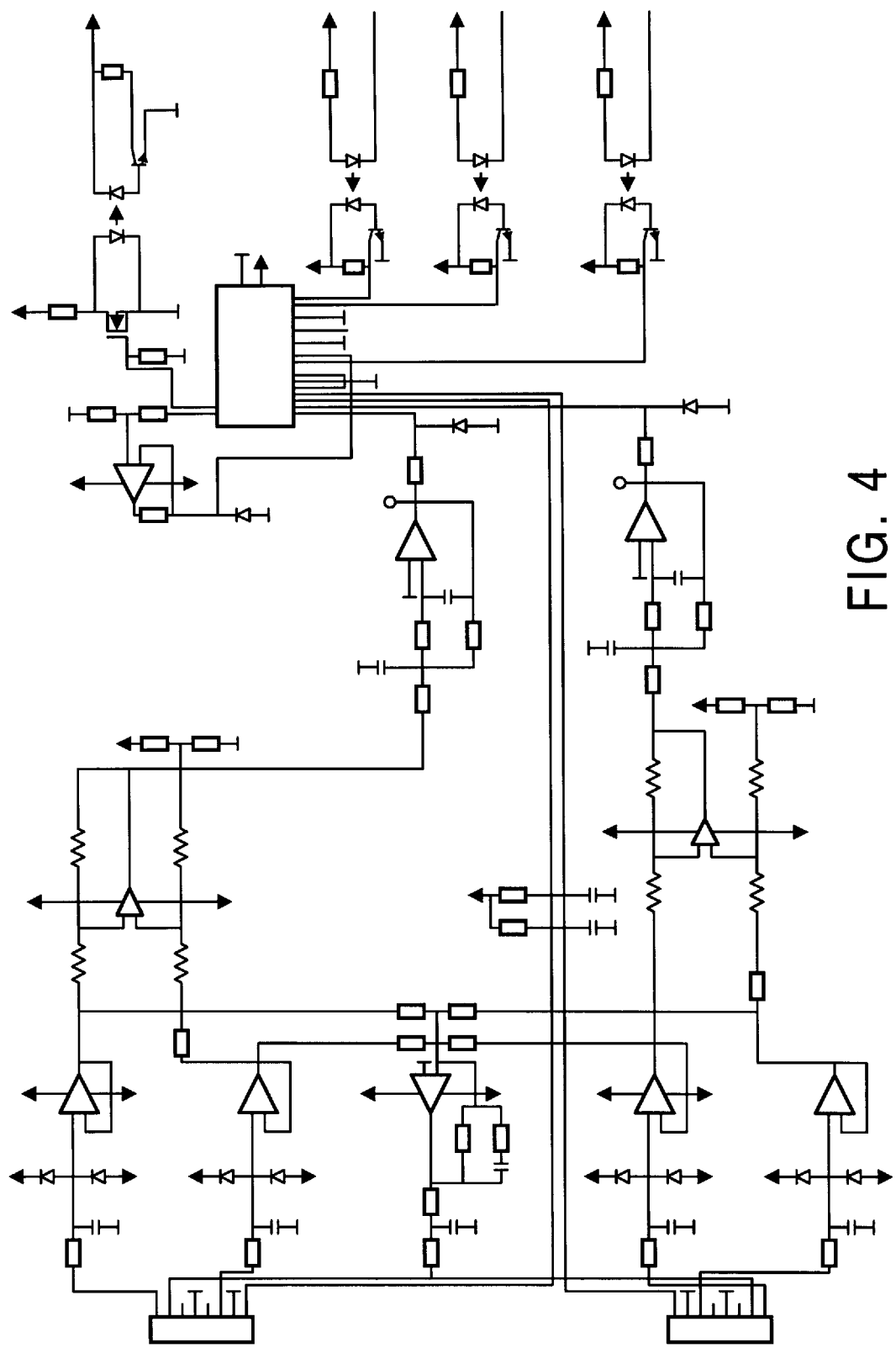
FIG. 4 is a more detailed circuit diagram of an analog or measuring part of a measuring instrument suitable for performing a process according to the present invention.

FIG. 4 shows the circuit diagram of the analog or measuring part for two coded sensors, in detail. The sensors are connected to the instrument by a multiple plastic plug connection and a highly flexible, shielded sensor cable. Each of these parts has a special code, which can be recognized by the instrument.

Figure 5A:
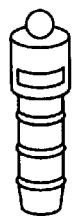
FIGS. 5a–5q show examples of connection pieces, connecting elements, or closure elements that are suitable for performing the process of the instant invention.
Figure 5B:
Figure 5C:
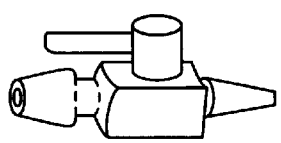
Figure 5D:
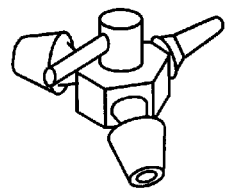
Figure 5E:
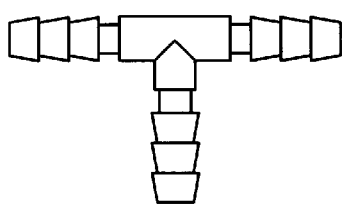
Figure 5F:
Figure 5G:
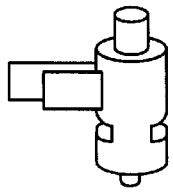
Figure 5H:
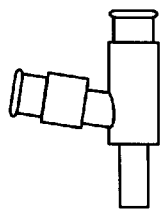
Figure 5I:
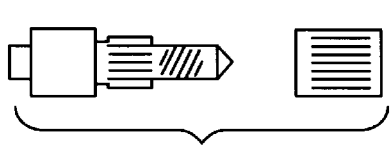
Figure 5K:
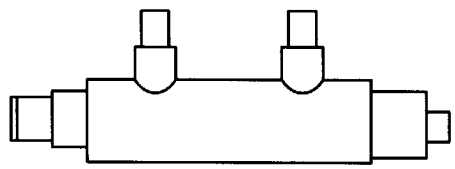
Figure 5L:
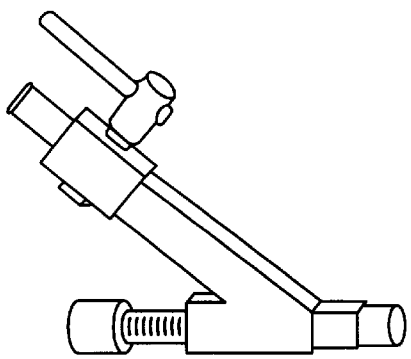
Figure 5M:
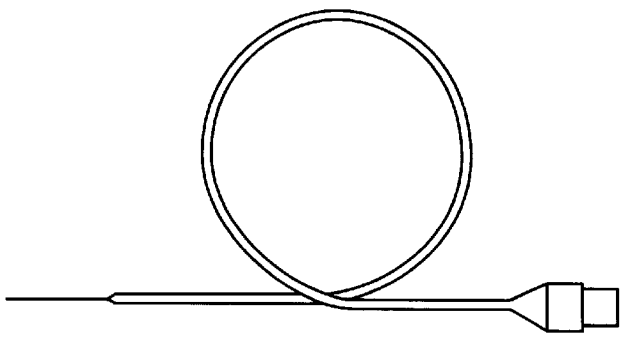

FIGS. 5a–5q show various embodiments for connection pieces and connecting elements or closure elements of the kind needed to perform the process of the invention. Connection pieces and connecting elements such as those shown, as well as connectors which are well-known in medical technology, according to the invention are provided with an electronically detectable code., At least one shielded electrical lead is provided with a suitable contact point, for producing an electrical connection between a code reader unit, which is independent or integrated into the measuring instrument; and the code-carrying element, which is embodied for instance, of a resistor element, a microchip, or other electronic components having a definable value or state.

FIGS. 6a, 6b, 6c, 6d, 6e, 6f(a), 6f(b), 6g(a), 6g(b), 6h(a), 6h(b), 6h(c), 6h(d), 6h(e), 6h(f), 6i(a), 6i(b), 6k(a), 6k(b), 6l(a), 6l(b), 6l(c), 6m(a), and 6m(b), and 6n show examples of sensors, and, in particular, electrode carriers for use in performing the process of the invention. Since the medical applications of the present invention are extremely numerous, the sensors may also have a great number of different forms and properties. The following list is therefore limited merely to several basic types, which in their embodiment can naturally be readily adapted to existing needs. In the variant shown in FIGS. 6f(a), 6f(b), 6g(a), 6g(b), 6k(a), 6k(b), 6l(a), 6l(b), and 6l(c), each electrode, or each measuring and/or therapy head, is guided individually. As a result of this embodiment, it is possible to place the various electrodes locally independently. This requires three individual electrode carriers for delivery and placement of the associated electrodes/measuring or therapy head.

In the variant of FIGS. 6m(a) and 6m(b), the electrodes are combined in one sensor. As a result, all of the electrodes are placed at the same location. The result is accordingly only a single sensor, with the associated electrode materials. This specialized embodiment also makes it possible to expose only the sensitive measuring electrodes during the taking of the desired measurement, and then to retract the electrodes back into the protective sheath during non-measurement times.

Figure 6N:
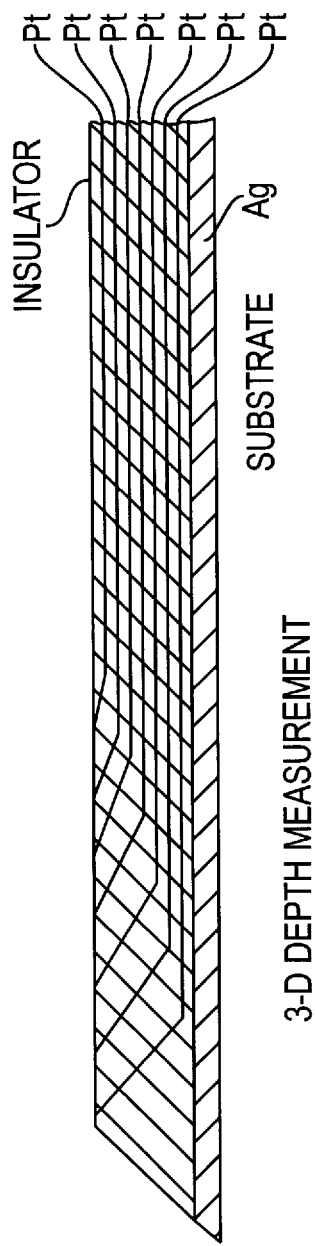
FIGS. 6a, 6b, 6c, 6d, 6e, 6f(a), 6f(b), 6g(a), 6g(b), 6h(a), 6h(b), 6h(c), 6h(d), 6h(e), 6h(f), 6i(a), 6i(b), 6k(a), 6k(b), 6l(a), 6l(b), 6l(c), 6m(a), and 6m(b), and 6n show examples of sensors that are suitable for performing the process of the present invention.

FIGS. 6a and 6n show a variant in which a plurality of electrodes are combined in one sensor. This embodiment makes three-dimensional measurement possible. Accordingly, there is only a single sensor with the associated electrode materials.

In the variant of FIGS. 6i(a) and 6i(b), a plurality of electrodes made of the same electrode material are accommodated in one sensor. This embodiment makes three-dimensional area measurement possible. The result is accordingly one area sensor with a plurality of measuring electrodes, and one neutral and one driving electrode each, along with the associated electrode materials.

It will be understood that many different types of electrodes may be used. For example, any and all of known membrane-covered electrodes, implantable electrodes for $H_2$, $O_2$ or bioelectrical signals, stick-on electrodes, surface electrodes, one-way electrodes, needle electrodes, and 3-D electrodes may be used. These electrodes can equally well be integrated into ultrasound sensors or catheters, such as venous catheters, central venous catheters, arterial catheters, cardiac catheters, balloon catheters, shunt measuring catheters, stenosis measuring catheters, liver catheters, Port-a-cath catheters, intracranial pressure catheters, drainage catheters, kidney/urine catheters, sensor catheters (for temperature, blood pressure, $H_2$, $O_2$, etc.), or in biopsy and aspiration instruments, of the kind also shown in FIGS. 5a–5q and 6a–6e.

Examples of electrode materials that have proved particularly suitable for the measuring tip are the following:

platinum, silver/silver chloride, silver, platinum-iridium, iridium, platinum-iridium-based, film electrodes, platinum-black-covered, microelectrodes, multibarreled electrodes, micropipette electrodes, tungsten, tungsten glass fibers, platinum-rhodium-quartz fibers, tantalum-on-sapphire multielectrodes, platinum-tantalum polyimides, and metal-noble metals. The substrate materials preferably used are polyamide, $p^+$-type silicone, n-type silicone, silicone rubbers, Kapton (polyimide), Pyrex, Teflon, Tri-Mil insulated silver wire, Dacron-mesh matrix, carbon, polyethylene, polyethylene glycol, polyurethane, borosilicates, epoxy resin, Hysol epoxy, Epoxylite, cyanoacrylate, stainless steel, Silastic, Parylene-N, polystyrene, polyepichlorohydrin, cellulose acetate membrane, and PVC membrane.

The sensors or therapy heads may also have transistors or other sensors as well as controllable valves.

All the sensors used in connection with the blood flow measuring instrument have integrated sensor detection. This encoding has the advantage that the instrument automatically recognizes the applicable sensor type, so that sensor-specific and measurement-type-specific software can be loaded. Furthermore, defective or incompatible products that produce incorrect measurements can be recognized.

The sensor can select a defined filter value in the measuring instrument. In the encoding, various circuitry embodiments are possible. First, when encoding with a resistor, a defined voltage potential is generated that is delivered to the microprocessor via A/D converters. The software processes the applicable signal and automatically selects the associated parameters. Second, when encoding with ASIC (customer-specific IC) a digitally enciphered signal is generated with the ASIC and is likewise delivered to the microprocessor. The microprocessor processes this signal and then again selects the associated parameters. If the code cannot be deciphered by the applicable reader or reader part, then an alarm signal can be tripped. These codes are likewise integrated into the catheters and other equipment, thereby insuring an unequivocal assignment to the sensor type.

Thus, the instrument (measuring and/or application and/or monitoring instrument) is capable of unequivocally recognizing the specifically coded electrode, micropipette, catheter, connecting element, and/or measuring and therapy head, and may be compatible and hence capable of operating only with it. The code can provide the suitably programmed base unit with information, such as, for example, electrode manufacturer, electrode type, electrode function, operativeness of the electrode, functional status of the electrode, location of the electrode, age of the electrode, segment or sector identification on the electrode or catheter, and electrode-specific baseline. With an active code element, it is even possible to encode the measurement signal itself. More simply, it is also possible for some of the measuring electronics, in miniaturized form, to be integrated with the applicable sensor and in particular with its measuring tip.

The code element may have a preamplifier for monitoring and control functions and is a component of the measuring and/or application sensor, micropipette, catheter, connecting element, and/or measuring and therapy head. The code element is located in the path between the measuring tip and the instrument and may be mounted directly on the sensor, micropipette or catheter, etc., or else is integrated directly with it. It can equally well be a component of the supply or outgoing lead or of a corresponding screw-type, plug-type or bayonet-type connection with the instrument. The code element may also be a component of the sheathing or jacket of the electrode, micropipette or catheter, and so forth, and has a direct connection with the electrode function, micropipette function or catheter function. That is, the code element takes on control functions for the particular application.

The advantages of the code are immediately apparent, and, according to the invention, reside in quality assurance, patient safety and reproduceability of the measurements, in particular long-term measurements. By means of the code, material properties can be defined as well as the location of the electrodes, micropipettes or catheters, and so forth, a basis for coordinate capability in multidimensional measured value or measurement subject display can be attained, the electrode-specific measured value range can be automatically defined, limitation of the electrolysis current or stimulation current (organ- or function-specific safeguarding) can be achieved, and electrode-specific calibration value specifications can be defined.

Independent of the foregoing, the encoding of medical technology utensils provides further advantage according to the invention. For instance, by use of encoded connecting pieces, the leads of conventional $H_2$ explosimeters can be checked and monitored for whether they are correctly sealed. Applications in technical fields, particularly in laboratory technology, veterinary medicine, etc., for instance, in combination with $CO_2$ sensors or other sensors, are within the competence of one skilled in the art. In particular, the measuring apparatus according to the invention can be combined with other equipment, such as equipment for the infusion of liquids and medicines. It will be understood that in this case the measuring electrodes can also be used as sensors for measuring the concentration of applied medications, such as vitamin C complexes, or for monitoring the pH value, glucose value, potassium value, and so forth.

Figure 7:
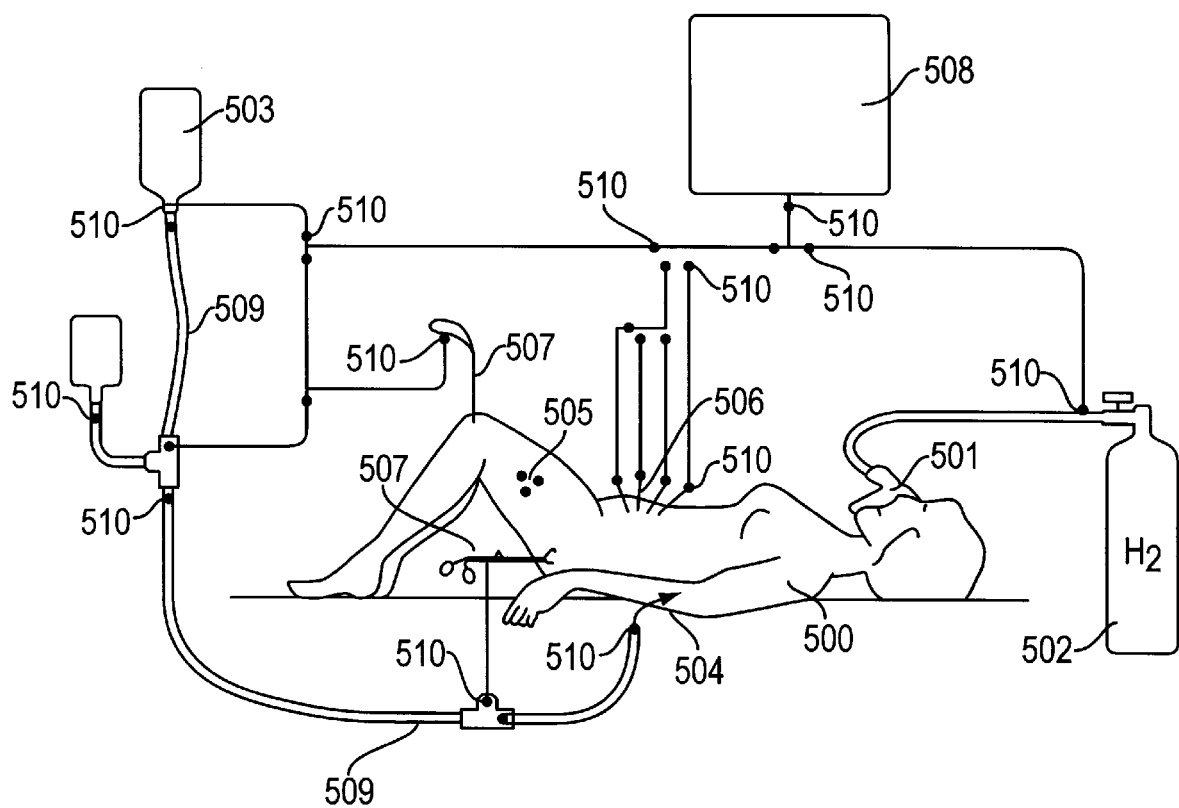
FIG. 7 shows an example of one possible measuring setup for performing the process according to the present invention.

The measuring array of FIG. 7 shows a patient 500, connected via a coded mask 501 to a hydrogen tank 502. An infusion bottle 503 is connected by suitable connecting elements to an infusion needle 504. Measuring sensors 506 and a surgical instrument 507 are likewise connected to the measuring instrument 508 via connecting elements with corresponding connection pieces. Implanted sensors 505 are provided with- an electromagnetic; readable code. All the utensils and instruments used are likewise provided with a code 510.

For long-term measurements, sensors with multiple electrodes are preferably used, and each of the electrodes for taking measurements extends from a protective sheath or jacket. The protective sheath or jacket may be formed of a resorbable material.

Further, the sensors are provided with means with which the electrodes can be bright sanded prior to each measurement. It will be understood that this process and means for it may also be employed in the technological and in industrial fields.

In a prepared embodiment, the sensors are connected to the measuring instrument via five-pole electric leads. In order not to have to provide a separate electric lead for each of the coded elements used, an I² C-bus circuit, an RS 485, or an ASB bus system may be used, for example, or the supply voltage for the active coded elements or a currently commercially available TSS 400 signal processor may be clocked, in order to send the measuring data over the same leads during the sleep mode of the supply voltage. PALs (programmable logic arrays) are also especially suitable for the encoding, because PALs make it possible to use merely a two-wire lead. Explicit reference is made here to the use of optical leads and electrooptical components for the reading and measuring part of the instrument.

Another preferred embodiment uses an integrated microprocessor for each coded element. This arrangement makes possible the handling of data transmission in the form of a logical ring, hereinafter described as "token ring $H_2$".

The token ring $H_2$ is sent by active participants to active participants in a numerically increasing order of participant addresses, with a token telegram. An exception is the participant having the highest address; it gives a token back to the central unit (which has the lowest address), to close the logical ring. When one active participant receives a token telegram, addressed to it, from its predecessor, then it is allowed to use the token and to handle message cycles. Its predecessor is determined on the basis of the entries in the list of active stations (LAS), which was generated after power-on in the list-token phase and later is updated continually upon receipt of a token telegram. If the token sender is not the registered predecessor, then the addressee must initially assume that an error has occurred and the addressee ignores the token. Not until an ensuing repetition from the same predecessor does acceptance occur, leading to token acceptance, since the receiver must assume that the logical ring has changed.

The receiver replaces a list of active stations (LAS) for the originally registered predecessors with the new list. After power-on, the software of the active participant changes to the list-token site, when the active participant is ready for the logical token ring. In this state, the active participant must listen on the line to ascertain which active participants are already in the logical token ring. To do that, all the token telegrams received are evaluated, and with the participant addresses contained in them the list of active stations (LAS) is generated. After two identical token cycles have been listened to in their entirety, the software still remains in this state until it is addressed by its predecessor with a request status. It must acknowledge with the status "ready for the ring" and then assume the active state. If a request status is received during the LAS generation, then it must acknowledge with the status "not ready for the ring". No other telegrams are processed in the list-token state; that is, they are neither acknowledged nor answered.

If, in detecting the active participants, the software recognized its own address in the source address of two token telegrams, then it must assume that a participant having the same address is already located in the ring. It must then change to the off-line state and send a report to the management (central unit).

If the software perceives no bus activity over a relatively long time, specifically during the time-out time, then it must conclude from this that the token was lost and that the logical ring must be rebuilt or restored, and it changes to the claim-token state.

The software assumes the claim-token state after the list-token state or active state if its time-out period has elapsed, or if no bus activity was ascertained during a certain period of time, and if it must be assumed that the token was lost. In that state, an attempt is made to reinitialize the logical ring or to start an initialization.

The central unit is capable at all times of monitoring the number of active participants using the list of active stations (LAS) and trips an alarm immediately if there is a change. With the management by means of a token ring as described above, the number of participants (hose, connecting piece, sensor, etc.) is not limited to a certain number either, and the various participants can be interconnected in an arbitrary order. As a result, it follows that for any conceivable connection, only one processor type is used, always with the same software, which naturally simplifies the manufacturing process considerably, The various components (hose, connecting piece, sensor, etc.) are then merely additionally loaded with some component-specific data. These data are stored in the EEPROM region of the processor and can accordingly be changed at any time as needed. One possible requirement for change would be a change of parameters because of empirical findings. These new parameters can then be loaded as a new software version (update) to the central unit. If components that have not been loaded with the most recent data are then incorporated into the logical ring, the central unit recognizes this from the version number, which once again is stored in memory each time in the processor of the various components, and can then change the entries in the corresponding EEPROM via the token ring as needed. This assures that even components that have not yet been loaded with the most recent parameters can still be used.

The central unit of the measuring instrument is thus capable at any time of monitoring the active codes. In this embodiment, the number of medical technology components used is not subject to any software-dictated limitation, and they can be connected in an arbitrary, that is, non-specified, order and combination without requiring that the software be adapted or changed. Thus not only can basic data of the various medical technology components be detected, but expiration dates, for instance from preserved blood supplies, can also be stored in memory and evaluated.

It will be understood that the above measuring and monitoring process can also be done in a multiplexing mode or is suitable for controlling medical manipulations, such as taking periodic tissue samples, administering medication, etc.

Although the invention has been described with reference to particular means, materials and embodiments, it is to be understood that the invention is not limited to the particulars disclosed and extends to all equivalents within the scope of the claims.

We claim:

1. A sensing device in combination with a medical technology apparatus, said device comprising:
   a detachable, coded sensor having at least one electrode or measuring head adapted to be placed in the region of a tissue to be studied and including at least one code value;
   a measuring instrument included with the medical technology apparatus;
   an associated code value detection unit;
   means for connecting said detachable, coded sensor to said measuring instrument via at least one coded connecting element, wherein said detachable, coded sensor is detachable from said coded connecting element;
   said measuring instrument including means for checking and reading said at least one code value of said coded sensor;

means for performing at least one first measurement of a parameter of the tissue; and means for storing at least one measured value obtained by said at least one first measurement, together with the at least one associated code value, in memory;

said coded sensor further comprising:
an electrode or measuring head carrier; and
an electrode or measuring head substrate;
wherein said electrode or measuring head carrier is supported by said electrode or measuring head substrate, and wherein said at least one code value is recognizable by said associated code value detection unit.

2. The device of claim 1, further comprising an electrical resistor element for storing said at least one recognizable code.

3. The device of claim 2, wherein at least part of an electronic circuitry used by said associated code value detection unit is located in said coded sensor.

4. The device of claim 1, further comprising a microchip for storing said at least one recognizable code.

5. The device of claim 4, wherein at least part of an electronic circuitry used by said associated code value detection unit is located in said coded sensor.

6. The device of claim 1, further comprising a transponder for sending said at least one recognizable code.

7. The device of claim 6, wherein at least part of an electronic circuitry used by said associated code value detection unit is located in said coded sensor.

8. The device of claim 1, further comprising an electrooptical component having means for sending said at least one recognizable code.

9. The device of claim 8, wherein at least part of an electronic circuitry used by said associated code value detection unit is located in said coded sensor.

10. The device of claim 1, wherein said electrode or measuring head carrier comprises a medical technology instrument.

11. The device of claim 1, comprising a plurality of electrodes or measuring heads.

* * * * *